United States Patent [19]

Akahane et al.

[11] Patent Number: 4,900,697

[45] Date of Patent: Feb. 13, 1990

[54] GLASS POWDERS FOR DENTAL GLASS IONOMER CEMENTS

[75] Inventors: Shoji Akahane, Higashikurume; Satoshi Tosaki, Omiya; Kazuo Hirota, Tokyo; Kentaro Tomioka, Chofu, all of Japan

[73] Assignee: G-C Dental Industrial Corporation, Tokyo, Japan

[21] Appl. No.: 150,299

[22] Filed: Jan. 29, 1988

[30] Foreign Application Priority Data

Feb. 13, 1987 [JP] Japan .................................. 62-29788

[51] Int. Cl.$^4$ ......................... C03C 3/23; C03C 3/247
[52] U.S. Cl. ........................................ 501/57; 501/63; 501/69; 501/70; 501/73; 106/35; 433/228.1
[58] Field of Search .................. 501/57, 63, 69, 70, 501/73; 106/35; 433/288.1

[56] References Cited

U.S. PATENT DOCUMENTS

| | | | |
|---|---|---|---|
| 4,123,416 | 10/1978 | Potter et al. | 106/35 X |
| 4,143,018 | 3/1979 | Crisp et al. | 501/57 X |
| 4,376,835 | 3/1983 | Schmitt et al. | 501/57 X |
| 4,378,248 | 3/1983 | Griffith | 501/57 X |
| 4,744,759 | 5/1988 | Bowen | 106/35 X |
| 4,775,592 | 10/1988 | Akahane et al. | 501/57 X |

FOREIGN PATENT DOCUMENTS 1477160 6/1977 United Kingdom .
2190372 11/1987 United Kingdom .

*Primary Examiner*—Mark L. Bell
*Assistant Examiner*—Karl Group
*Attorney, Agent, or Firm*—Oblon, Spivak, McClelland, Maier & Neustadt

[57] ABSTRACT

A fluoroaluminosilicate glass powder for dental glass ionomer cements has a specific gravity of 2.4 to 3.5 and a mean particle size of 0.02 to 10 $\mu$m, contains in its components 20 to 50% by weight of $SiO_2$, 20 to 40% by weight of $Al_2O_3$, 15 to 40% by weight of SrO, 1 to 20% by weight of $F_2$ and 0 to 15% by weight of $P_2O_5$ on the converted oxide basis, and is substantially free from alkali metal ions such as Li, Na, K, Rb and Cs ions, and Be, Mg (and Ca) and Ba ions of alkali earth metal ions. For further improvements in physical properties, 100 parts by weight of the glass powder are surface-treated with 0.01 to 5 parts by weight of an acid and/or a fluoride.

6 Claims, No Drawings

4,900,697

GLASS POWDERS FOR DENTAL GLASS IONOMER CEMENTS

BACKGROUND OF THE INVENTION

1. Field of the Invention

The present invention relates to dental cements and, in particular, to dental glass ionomer cements. More specifically, the present invention is concerned with fluoroaluminosilicate glass powders designed for use as dental glass ionomer cements.

2. Statement of the Prior Art

Dental glass ionomer cements are basically obtained by allowing an acid component composed mainly of polyacrylic acid to react with fluoroaluminosilicate glass powders in the presence of water for setting, and are one of the materials which have been widely used in the dental field. With the glass ionomer cements characterized in that they are of very excellent biocompatibility, show chemical bond to tooth substance and provide a hardened mass which is translucent and of excellent estheticity, they are further expected to reinforce or strengthen tooth due to the fluorine contained therein. Because of their outstanding advantages the glass ionomer cements have been widely used for many purposes, like restorative filling, cementation of crowns, inlays and bridges or orthodontic bands, lining of cavities, core build-up and pits and fissure sealing.

However, only a combination of aluminosilicate glass powders with polyacrylic acid produces cement paste, poor in both flow and working property. In addition, since the cement requires a long time for complete set, it disintegrates on the surface when contact with saliva or water in a patient mouth and becomes brittle, thus failing to produce its final strength and estheticity. As well-known in the previous report, numerous methods have been investigated so as to overcome these disadvantages. For instance, Japanese Patent Laid-Open No. 52(1977)-101893 for public inspection discloses a setting liquid containing a 45 to 60% aqueous solution of polyacrylic acid or acrylic copolymer and one or more of polybasic carboxylic acids in an amount 7 to 25% of the total weight. With this liquid, higher reaction rates and improved crushing strength were achievable. Japanese Patent Laid-Open No. 57(1982)-2210 for public inspection discloses a setting liquid for glass ionomer cements which contains tartaric acid and a fluoro complex salt with an acrylic acid copolymer, and is found to produce the aforesaid effects and result in less solubility. On the other hand, Japanese Patent Application No. 60(1985)-206299 discloses dental glass ionomer cements containing glass powders treated on the surfaces with a fluoride, and shows that a cement paste just after mixing is improved in its flow as well as in mixing property.

As stated in the foregoing, various investigations have been made on improvements in dental glass ionomer cements, but the dental cements developed by now are foound to have many disadvantages and to be far from the ideal. For instance, while the solubility of dental zinc phosphate cements to distilled water is about 0.03%, as measured according to JIS T 6602, that of glass ionomer cements are 0.2% and more. In this respect, there is left much to be modified. When glass ionomer cements are actually applied in the mouth for clinical purposes, reduction of their solubility seems indispensable for their better durability in the mouth. In the case of current glass ionomer cements, a cement-surface embrittling phenomenon, which is believed to correlate with the solubility, occurs when they contact with saliva in an earyl stage of the process of setting. The surface of cement, which is not completely hardened, is easily affected by water, and dissolve therein, thus offering a problem of losing its translucency. This problem leads to a grave defect in view of aestheticity, when that cement is used for restorative filling. For that reason, it is necessary to apply a varnish capable of being resistant to water on the surface of cement just after filling so as to shut off the influence of water. Further, hardened cements have had somewhat improved crushing strength, but have still been insufficient, compared with that of tooth substance. There is thus an increasing demand toward further improving its crushing strength.

Referring to the general properties of dental materials supplied to clinicians in the form of half-made products, working time should be preferably long and, contrary, setting time should be short. In other words, cement paste should preferably retain flowability for only the required time, and be set as sharply as possible. However, current glass ionomer cements are still far from ideal in this regard.

SUMMARY OF THE INVENTION

As a result of investigations made on the fluoroaluminosilicate glass powders used for dental glass ionomer cements with a view to improve in the foregoing points, it has unexpectedly been found that certain glasses containing no alkali metal fit for the object of the present invention.

According to one aspect of the present invention, there is provided a fluoroaluminosilicate glass powder for dental glass ionomer cements, which has a specific gravity of 2.4 to 3.5 and a mean particle size of 0.02 to 10 μm and which, in its components, contains 20 to 50% by weight of $SiO_2$, 20 40% by weight of $Al_2O_3$, 15 to 40% by weight of SrO, 1 to 20% by weight of $F_2$ and 0 to 15% by weight of $P_2O_5$ on the converted oxide basis, and is from alkali metal ions such as Li, Na, K, Rb and Cs ions, and Be, Mg and Ba ions of earth metal ions. The glass powder according to the first aspect of the present invention is found to be of less solubility, to excel in water resistance and to be very low in the sensitivity to water in the initial stage of setting. Further, a glass ionomer cement obtained using the present glass powders has a sufficient working time, namely a sufficient time allowed for manipulation, and sets more rapidly. Still further, this glass ionomer cement has many other advantages inclusive of improvements in physical properties such as crushing strength, and radio-opacity are imparted thereto.

According to another aspect of the present invention, there is provided a glass powder in which CaO is excluded from the glass powder according to the first aspect of the invention. That is, there is provided a fluoroaluminosilicate glass powder for dental glass ionomer cements, which has a specific gravity of 2.4 to 3.5 and a mean particle size of 0.02 to 10 μm and which, in its components, contains 20 to 50% by weight of $SiO_2$, 20 to 40% by weight of $Al_2O_3$, 15 to 40% by weight of SrO, 1 to 20% by weight of $F_2$ and 0 to 15% by weight of $P_2O_5$ on the converted oxide basis, and is free from alkali metal ions such as Li, Na, K, Rb and Cs ions, and Be, Mg, Ca and Ba ions of alkaline earth metal ions. A glass ionomer cement making use of this glass powder is found to be much more improved in the aforesaid effects. The glass ionomer cement making use of the Ca-free glass powder is much more improved in the water resistance, sensitivity to water in the initial stage of setting, mixing manipulation, setting properties, radio-opacity and physical properties.

According to yet another aspect of the invention, there is provided a fluoroaluminosilicate glass powder for dental glass ionomer cements, which is characterized in that the glass powder, according to the first or second aspect of the invention, is treated on the surface with an acid and/or a fluoride in an amount of 0.01 to 5 parts by weight with respect to 100 parts by weight thereof.

In addition to the effects such as improvements in solubility and decrease of sensitiblity to water in the initial stage of setting, glass ionomer cements containing the glasss powders surface-treated according to the present invention are effective in further improving the flowability and, hence, mixing manipulation of cement paste.

Dental glass ionomer cements, in which the fluoroaluminosilicate glass powders of the present invention are used, are decreased in solubility but improved in durability, as already mentioned. In addition, the glass ionomer cements is decreased in the sensitivity to water in the initial setting just after mixing.

The setting properties of glass ionomer cements are extremely improved and the flowability of cement pastes are sustained over an increased time length, so that their setting proceeds more rapidly. Therefore, clinical manipulations for luting, filling, etc. can be carried out satisfactory with sufficient time. Further, the glass ionomer cements combine much more improved physical properties such as higher crushing strength and resistance to disintegration with radio-opacity. Still further, the flowability of cement pastes is sufficient.

DETAILED DESCRIPTION OF PREFERRED EMBODIMENT

It is desired that the galss powder used in the present invention has a true specific gravity in a range of 2.4 to 3.5. The true specific gravity of glass powders may be measured by usually employed methods using a specific gravity bottle. When the powder has a specific gravity of 2.4 or less, its weight beomes too light to be mixed with the liquid, so that difficulty is encountered in mixing. For that reason, the powder should preferably have a specific gravity exceeding 2.4. When the powder has a specific gravity of greater than 3.5, on the other hand, the proportion of $Al_2O_3$, $SiO_2$ and $F_2$, having an influence upon reactivity, departs from the preferred scope of the present invention, thus resulting in a less reactivity. It is therefore preferred that the specific gravity of the glass powder is 2.4 to 3.5 inclusive.

In the present invention, it is required that the glass powders is 10 to 0.02 $\mu$m in the mean particle size. The use of glass powders having a mean particle size exceeding 10 $\mu$m is disadvantageous, since they cause misfit of a precision cast crown when used as a luting cement. In this case, a crown, inlay or bridge is seated excessively away from tooth cavity. This makes occlusal equilibration difficult and has an unfavorable influence upon the durability of the cement in the mouth. Also, when powders having a mean particle size more than 10 $\mu$m are used for restorative filling, a problem arises in connection with a contact feeling, since it is impossible to obtain the desirable surface smoothness of the filled material by usual polishing method. Further, the setting reaction of such powders with a liquid is so slow that their sensitivity to water in the initial stage of setting becomes higher. For these reasons, the glass powders should have a mean particle size of 10 $\mu$m or less. With fine glass powders having a mean particle size of 0.02 $\mu$m or less, on the other hand, mixing manipulation drops to an extreme so that it is very difficult to realize effective mixing. This means that the powder to liquid ratio decrease as a result of difficulty involved in the incorporating and mixing of powder with liquid. For these reasons, the mean particle size of the glass powders used is limited to 0.02 to 10 $\mu$m inclusive. Direct measurement of the mean particle size of glass powders may easily be achieved with an electron microscope. By the term "particle size" is here meant the so-called averaged long-to-short diameter value of particles.

The aluminosilicate glass powders generally used in the glass ionomer cements are a so-called silicate glass. Due to the structure in which Al is replaced at the Si position, the presence of metal ions is essentially required for electric balance. Of these metal ions, alkali metal ions are especially effective for reduction in the melting points of glasses, and also make it easy to make glasses. It has been found, however, that the alkali metal ions give an unfavorable influence upon the nature of glass ionomer cements. For instance, it has been noted that a hardened mass of glass ionmer cements making use of glass powders containing these metal ions shows a high solubility in water. In other words, such glass powders are responsible for deteriorations in water resistance, when used in the mouth. Hence, a glass ionomer cement, which contains glass powders free from such alkali metal ions, extremely decreases in solubility. This implies that when such a cement is applied in the mouth cavity over a long period, favorable results are obtained in connection with the retention and water resistance of the hardened cement. The sensitivity of the cement to water in the initial stage of setting was also reduced by the removal of alkali metal ions. Consequently, even when the cement surface comes into contact with water during the initial setting, a surface-clouding phenomenon leading to deteriorations in translucency and aesthetic characteristics can substantially be suppressed.

In the present invention, therefore, the content of alkali metal ions such as Li, Na, K, Rb and Cs ions is substantially nil. In other words, alkali metal compounds cannot intentionally be used as the raw material for making glasses according to the present invention. The fluoroaluminosilicate glass powders free from alkali metal ions according to the present invention also have a favorable influence upon setting characteristics. It is thus possible to increase the time length during which a cement paste keeps its sufficient flow, i.e., the working time. Conversely speaking, the glass ionomer cements including alkali metal ion-containing glass powders is short in the working time, since the viscosity of a cement paste obtained therefrom just after mixing increases rapidly.

In general, the alkaline earth metal ions contained in glass powders react more rapidly than the aluminum ions do in the course of setting of glass ionomer cements. Hence, the alkaline earth metal ions take noticeable part in the initial reaction stage. Since $Ba^{2+}$ ions are known to possess toxicity, however, it is disadvantageous to add them to the reactants in the glass powders of dental glass ionomer cements in the present invention, which are one of biomaterials. When Be and Mg ions are added to the aluminosilicate glass of the present invention, its setting reaction is so retarded that any sharp setting characteristics are not expected. Further, various physical properties also deteriorate. Suitable for such alkaline earth metal ions are Ca and Sr ions, but preference is given to Sr ions. The aluminosilicate glass containing Sr ions, rather than Ca ions, undergoes sharper setting reaction and excels in various physical properties including crushing strength. In the present invention, Sr ions are an essential component. Ca ions may not necessarily be added. The aluminosilicate glass containing Sr ions has an additional advantage of imparting radio-opacity thereto. The radio-opacity are important in the diagnosis of prognosis, because it is required to confirm the locations for filling, lining, etc., when the cement is used for such purposes.

The glass according to the present invention should be composed mainly of Si, Al, Sr, F and O ions and, preferably, contain P ions. In the present disclosure, as usual with the case where the composition of glasses is generally expressed in terms of percent by weight, ions such as Si, Al, Sr and P ions except for F ions are converted to their oxides and F ions are done as such. The percentages of the respective ions in the composition are then defined on the basis of the total weight of 100%. Therefore, the main components of the present invention are $SiO_2$, $Al_2O_3$, SrO, $P_2O_5$ and $F_2$.

In the glass composition of the present invention, the proportion of $SiO_2$ amounts to 20 to 50% by weight of the total weight of the glass powders.

Containing $SiO_2$ in a proportion of greater than 50% by weight, glass compositions are decreased in both strength and reactivity, and are thus cannot be used as part of glass ionomer cements. Further, the hardened mass are increased in solubility and poor in water resistance. Glass compositions containing $SiO_2$ in an amount of below 20% by weight render glass-making difficult, and provide glass ionomer cements which are rather increased in solubility and, hence, decreased in strength. The raw materials of $SiO_2$ mainly include silica sand ($SiO_2$), kaolin ($Al_2O_3.2SiO_2.2H_2O$) and the like.

In the glass compositions of the present invention, the proportion of $Al_2O_3$ ranges from 20 to 40% by weight of the total weight of the glass powders. Containing $Al_2O_3$ in an amount of below 20% by weight, glass compositions provide glass ionomer cements which set at a very slow reaction rate and, once set, deteriorate in physical properties. Glass compositions having an $Al_2O_3$ content of greater than 40% by weight have too high melting point, and provide dental cements which are poor in translucency and aesthetic properties. Hence, the compositional range of $Al_2O_3$ is limited to a range of 20 to 40% by weight of the total weight of the glass powders.

The raw materials of $Al_2O_3$ may include, for instance, alumina ($Al_2O_3$), aluminum hydroxide [$Al(OH)_3$], kaolin ($Al_2O_3.2SiO_2.2H_2O$), aluminum fluoride ($AlF_3$), aluminum phosphate ($AlPO_4$) and the like.

The proportion of SrO used in the present invention is limited to a range of 15 to 40% by weight based on the total weight of the glass powders. Glass compositions containing SrO in an amount of below 15% by weight render cement paste less active and glass-making difficult. Also, there is found a lowering of radio-opacity. Glass compositions containing SrO in an amount of greater than 40% by weight again make glass-making difficult, and provide dental cements which should be manipulated within a shorter time, are decreased in physical properties, and cannot practically be used. The raw materials of SrO, used in the present invention may include strontium carbonate ($SrCO_3$), strontium hydroxide [$Sr(OH)_2$], strontium oxide (SrO), strontium fluoride ($SrF_2$), strontium phosphate [$Sr_3(PO_4)_2$] and the like.

In the present invention, the proportion of $F_2$ is limited to a range of 1 to 20% by weight based on the total weight of the glass powders. Glass compositions having a fluorine content of below 1% by weight show too high a glass melting point. Flourine is required for glass melting. In other words, fluorine is very effective for lowering the melting point of glasses, and acts as a flux. In an amount of below 1% by weight, fluorine has no marked effect upon a lowering of the melting point of glasses. In an amount of below 1% by weight, the reactivity of the powders also drops. When fluorine ($F_2$) is incorporated into glass compositions in an amount of greater than 20% by weight, on the other hand, the reactivity of the glass powders again drops so that the resulting hardened cements are decreased in physical properties. The cements are also increased in solubility. For these reasons, the fluorine content is limited to the range of 1 to 20% by weight. The raw materials of fluorine may include strontium fluoride ($SrF_2$), aluminium fluoride ($AlF_3$) and the like.

Phosphates may be used so as to lower the melting points of glasses, but may not necessarily be added to glass compositions. It is to be noted, however, that the phosphates may serve to increase a working time of cement pastes. For that reason, the phosphates may preferably be added to glass compositions in a certain amount so as to improve the mixing manipulation of cement paste. However, the incorporation of the phosphate in an amount of greater than 15% by weight, calculated as $P_2O_5$, is unsuitable, since the setting reaction proceeds too slowly for dental cements. Hence, the proportion of the phosphate is limited to a range of 0 to 15% by weight, calculated as $P_2O_5$. The raw materials of $P_2O_5$ may include, for example, aluminium phosphate ($AlPO_4$), strontium phosphate [$Sr_3(PO_4)_2$] and the like.

As stated in the foregoing, the aluminosilicate glasses of the present invention contain $SiO_2$, $Al_2O_3$, SrO, $F_2$ and $P_2O_5$ as the main components, and are substantially free from neither alkali metal ions such as Li, Na, K, Rb and Cs ions nor alkali earth metal ions such as Be, Mg and Ba ions. It is to be understood, however, that any limitation is not imposed upon other elements. As already detailed, the proportions of $SiO_2$, $Al_2O_3$, SrO, $F_2$ and $P_2O_5$ affect diverse aspects such as the working time, the initial setting time, physical properties such as solubility, translucency and specific gravity. The raw materials of such substances are not limited to the aforesaid ones, and may be preestimated and formulated based on the calculation for formulation. What is essential in the present invention is that the critical components in glasses may come under the scope defined by the present invention.

The glass powders of the present invention may be obtained by melting the raw materials, cooling and then pulverizing it in a conventional manner. For instance, the raw materials may be weighed and blended together, molten at a higher temperature exceeding 1000° C., cooled off in the air, and pulverized with a ball mill, etc. More preferably, the resulting powders may be passed through a sieve so as to remove larger particles. Usually, the powders may be passed preferably through an 80# sieve, or more preferably through an 120-mesh sieve.

For the acids used for surface treatment according to the present invention, mentioned are phosphoric acid, hydrochloric acid, pyrrophosphoric acid, tartaric acid, citric acid, glutaric acid, malic acid, acetic acid, etc. For the same purpose, monobasic or dibasic phosphates that are acidic substances may also be used. For fluorides used for surface treatment according to the present invention, the fluorides disclosed in Japanese Patent Application No. 60(1985)-206229 may be used. If the aluminosilicate glass powders free from containing alkali metal ions and a part of alkali earth metal ions, such as those disclosed in the present invention, are surface-treated with these acids and/or fluorides, not only are the physical properties improved, but the flowability and manipulatability of cement paste are also enhanced. Thus, when the aluminosilicate glasses disclosed in the present invention are surface-treated with the acids and/or fluorides, the obtained dental glass ionomer cements are much more improved in performance over the known dental cements. In view of the physical properties, the fluorides are preferred to the acids. It is a matter of course that the aluminosilicate glasses may be treated simultaneously or successively with the acids and fluorides. The surface treatment may be achieved by mechanical mixing with a mill, etc. Alternatively, the acids or fluorides may be dissolved in distilled water or some solvents, which are then mixed with the glass powders, followed by the removal thereof by drying.

As the polymer acids used in combination with the glass powders of the present invention, when preparing dental glass ionomers, use may be made of the known liquids for glass ionomer cements. For instance, polyacrylic acid, acrylic acid copolymers, polymaleic acid, etc. may be used. In addition, the known improved setting liquids may be used as well. For example, particular preference is given to the setting liquids containing polybasic carboxylic acids disclosed in Japanese Patent Laid-Open No. 52(1977)-101893. These polymer acids or polybasic carboxylic acids may partly or wholly be powdered and mixed with the glass powders of the present invention for practical purposes. In this case, any problem will not arise, if mixing is carried out in the presence of a suitable amount of water.

EXAMPLES

The present invention will now be explained in further detail with reference to the following examples annd comparative exmaples.

Example 1

Sufficiently mixed in a mortar were 25.6 g of aluminum hydroxide [$Al(OH)_3$], 37.4 g of silica sand ($SiO_2$), 2.1 g of strontium carbonate ($SrCO_3$), 11.0 g of aluminum fluoride ($AlF_3$) and 23.9 g of strontium phosphate [$Sr_3(PO_4)_2$]. After mixing, the mixture was put in a porcelain crucible, which was then fixed in an electrical furnace. The furance was brought up to 1200° C., and was constantly controlled at that temperature for 3 hours. After air-cooling, the product was pulverized in a ball mill for 20 hours. The powders were passed through an 120-mesh sieve to obtain cement powders found to have a specific gravity of 2.68 and a mean particle size of 3.4 $\mu$m. The cement powders were then mixed with a commercially available setting liquid for glass ionomer cements (Fuji Ionomer Type I Liquid sold from G-C Dental Industrial Corp. and produced under batch No. 120641) in a proportion of 1.8 g to 1.0 g for the measurement of physical properties. The initial setting time, crushing strength and rate of disintegration were measured according to JIS T-6602 for dental zinc phosphate cement. The working time was determined by making the end of a spatula contact with a surface of a mixed cement paste. The rate of disintegration just after the initial setting was measured between 10 minutes and 60 minutes after the start of mixing according to JIS T-6602. Ten minutes after the commencement of mixing, the hardened cement was immersed in distilled water, and pulled up therefrom after 60 minutes. To measure the flowability of a cement paste, an 120-gram load was applied to 0.5 ml of the cement paste by the method for the measurement of standard consistency according to JIS T-6602, and the diameter (averaged long-short diameter) of the cement paste thus spread was measured. However, it was 1.5 minutes after the commencement of mixing that the load was applied to the cement paste. Thus measured consistency, working time, initial setting time, crushing strength, rate of disintegration and rate of disintegration just after the initial setting were 30 mm, 2 minutes 55 seconds, 5 minutes 15 seconds, 1650±80 Kg/cm$^2$, 0.09% and 0.52%, respectively. The cement is thus found to provide an excellent dental luting cement.

Example 2

Sufficiently mixed in a mortar were 34.0 g of kaolin ($Al_2O_3.2SiO_2.2H_2O$), 25.8 g of strontium carbonate ($SrCO_3$), 15.6 g of aluminum phosphate ($AlPO_4$), 13.3 g of aluminium fluoride ($AlF_3$) and 11.3 g of silica sand ($SiO_2$). After mixing, the mixture was put in a platinum crucible, which was then heated in an electrical furnace. After heating, the furnace was kept constant at an in-furnace temperature of 1250° C. for 3 hours. After melting, the melt was cooled off in the air, pulverized in a ball mill for 25 hours, and was passed through an 120-mesh sieve to obtain cement powders which were found to have a specific gravity of 2.77 and a mean particle size of 2.8 $\mu$m. The cement powders were then mixed with a commercially available setting liquid for glass ionomer cements (Fuji Ionomer Type I Liquid sold from G-C Dental Industrial Corp. and produced under batch No. 120641) in a proportion of 1.8 g to 1.0 g. Thus measured consistency, working time, initial setting time, crushing strength, rate of disintegration and rate of disintegration just after the initial setting, measured by the procedure of Ex. 1, were 31 mm, 3 minutes 05 seconds, 5 minutes 15 seconds, 1780±90 Kg/cm$^2$, 0.07% and 0.42%, respectively. The cement was thus found to provide an excellent dental luting cement.

Example 3

Sufficiently mixed in a mortar were 52.3 g of kaolin ($Al_2O_3.2SiO_2.2H_2O$), 31.9 g of strontium fluoride ($SrF_2$), 8.3 g of aluminum phosphate ($AlPO_4$) and 7.5 g of silica sand ($SiO_2$). After mixing, the mixture was put in a platinum crucible, which was then heated in an electrical furnace. After heating, the furnace was kept constant at an in-furnace temperature of 1280° C. for 3 hours. After melting, the melt was cooled off in the air, pulverized in a ball mill for 20 hours, and was passed through an 120-mesh sieve to obtain cement powders which were found to have a specific gravity of 2.87 and a mean particle size of 2.9 $\mu$m. The cement powders were then mixed with a commercially availalbe setting liquid for glass ionomer cements (Fuji Ionomer Type I Liquid sold from G-C Dental Industrial Corp. and produced under batch No. 120641) in a proportion of 1.8 g to 1.0 g. Thus measured consistency, working time, initial setting time, crushing strength, rate of disintegration and rate of disintegration just after the initial setting, measured by the procedures of Ex. 1, were 30 mm, 3 minutes 00 second, 5 minutes 15 seconds, 1750±80 Kg/cm$^2$, 0.08% and 0.45%, respectively. The cement was thus found to provide an excellent dental luting cement.

Example 4

Sufficiently mixed in a mortar were 45.4 g of kaolin ($Al_2O_3.2SiO_2.2H_2O$), 8.1 g of silica sand ($SiO_2$), 20.2 g of strontium oxide ($SrCO_3$), 8.8 g of calcium fluoride ($CaF_2$), 6.8 g of aluminum fluoride ($AlF_3$) and 10.7 g of calcium hydrogen phosphate ($CaHPO_4.2H_2O$). After mixing, the mixture was put in a porcelain crucible, which was fixed in an electrical furnace. The furnace was increased in temperature, and was controlled at a constant temperature of 1150° C. for 5 hours. After cooling off in the air, the melt was pulverized in a ball mill for 20 hours, and was passed through an 120-mesh sieve to obtain cement powders which were found to have a specific gravity of 2.61 and a mean particle size of 3.2 μm. The cement powders were then mixed with a commercially available setting liquid for glass ionomer cements (Fuji Ionomer Type I Liquid sold from G-C Dental Industrial Corp. and produced under batch No. 120641) in a proportion of 1.8 g to 1.0 g. Thus measured consistency, working time, initial setting time, crushing strength, rate of disintegration and rate of disintegration just after the initial setting, measured by the procedures of Ex. 1, were 29 mm, 2 minutes 35 seconds, 5 minutes 30 seconds, 1580±60 Kg/cm$^2$, 0.12% and 0.65%, respectively. The cement was thus found to provide an excellent dental luting cement.

Examples 5 to 8

One hundred (100) g of the glass powders prepared in each of Examples 1 to 4 were mixed with 100 g of a 1% aqueous solution of potassium hexafluorotitanate to make a slurry, which was then surface-treated by drying it in a dryer having a temperature of 120° C. for the evaporation of moisture. The thus obtained respective powders were then mixed with a commercially available setting liquid for glass ionomer cements (Fuji Ionomer Type I Liquid sold from G-C Dental Industrial Corp. and produced under batch No. 120641) in a proportion of 1.9 g to 1.0 g to measure consistency, working time, initial setting time, crushing strength, rate of disintegration and rate of disintegration just after the initial setting by the procedures of Ex. 1. The results are set out in Table 1, and indicates that the cements are not only excellent as a luting cement, but are superior in manipulatability to the those of Examples 1 to 4, which were not subjected to any surface treatment.

TABLE 1

| Example No. | Consistency (mm) | Working time (min. sec.) | Initial setting time (min. sec.) | Crushing strength (kg/cm$^2$) | Rate of disintegration (%) | Rate of disintegration just after initial setting (%) |
| --- | --- | --- | --- | --- | --- | --- |
| 5 | 34 | 3 min. 30 sec. | 5 min. 30 sec. | 1960 ± 90 | 0.07 | 0.41 |
| 6 | 35 | 3 min. 35 sec. | 5 min. 30 sec. | 2020 ± 100 | 0.06 | 0.32 |
| 7 | 34 | 3 min. 30 sec. | 5 min. 30 sec. | 2010 ± 100 | 0.06 | 0.35 |
| 8 | 32 | 3 min. 05 sec. | 5 min. 45 sec. | 1820 ± 80 | 0.10 | 0.50 |
| 9 | 35 | 3 min. 35 sec. | 5 min. 45 sec. | 1920 ± 100 | 0.09 | 0.40 |
| 10 | 33 | 3 min. 10 sec. | 6 min. 00 sec. | 1750 ± 70 | 0.13 | 0.55 |

Examples 9 and 10

One hundred (100) g of the glass powders prepared in each of Examples 3 and 4 were mixed with 100 g of a 1% aqueous solution of aluminum dihydrogenphosphate [$Al(H_2PO_4)_3$]. Each of the thus obtained slurries was then surface-treated by drying it in a dryer having a temperature of 120° C. for the complete evaporation of moisture. The thus obtained respective powders were then mixed with a commercially available setting liquid for glass ionomer cements (Fuji Ionomer Type I Liquid sold from G-C Dental Industrial Corp. and produced under batch No. 120641) in a proportion of 1.9 g to 1.0 g to measure consistency, working time, initial setting time, crushing strength, rate of disintegration and rate of disintegration just after the initial setting by the procedures of Ex. 1. The results are also set out in Table 1. The cements were found to provide excellent dental luting cement.

Examples 11 to 14

The glass powders surface-treated as in Examples 5 to 8 were mixed with a commercially available setting liquid for glass ionomer cements (Fuji Ionomer Type II (for filling) Liquid sold from G-C Dental Industrial Corp. and produced under batch No. 220641) in a proportion of 2.7 g to 1.0 g to measure the physical properties as in Example 1. The results are set out in Table 2. It is noted that the consistency was determined under a load of 2.5 Kg.

In consequence, the cements obtained in these examples were found to be excellent as the glass ionomer cements for filling.

TABLE 2

| Example No. | Consistency (mm) | Working time (min. sec.) | Initial setting time (min. sec.) | Crushing strength (kg/cm$^2$) | Rate of disintegration (%) | Rate of disintegration just after initial setting (%) |
| --- | --- | --- | --- | --- | --- | --- |
| 11 | 31 | 3 min. 15 sec. | 4 min. 00 sec. | 2260 ± 110 | 0.05 | 0.31 |
| 12 | 33 | 3 min. 25 sec. | 4 min. 00 sec. | 2370 ± 120 | 0.04 | 0.22 |
| 13 | 32 | 3 min. 15 sec. | 4 min. 00 sec. | 2320 ± 120 | 0.04 | 0.25 |

TABLE 2 -continued

| Example No. | Consistency (mm) | Working time (min. sec.) | Initial setting time (min. sec.) | Crushing strength (kg/cm$^2$) | Rate of disintegration (%) | Rate of disintegration just after initial setting (%) |
| --- | --- | --- | --- | --- | --- | --- |
| 14 | 30 | 2 min. 50 sec. | 4 min. 15 sec. | 2100 ± 110 | 0.08 | 0.36 |

Comparative Example 1

Sufficiently mixed in a mortar were 40 g of silica sand (SiO$_2$), 26 g of alumina (Al$_2$O$_3$), 12 g of sodium fluoride (NaF), 15 g of calcium carbonate (CaCO$_3$) and 7 g of calcium phosphate [Ca$_3$(PO$_4$)$_2$]. After mixing, the mixture was put in a porcelain crucible, and was molten at 1150° C. for 3 hours in an electrical furnace. After melting, the melt was cooled off in the air, pulverized in a ball mill for 20 hours, and was passed through an 120-mesh sieve to obtain cement powders. The cement powders were then mixed with a commercially available setting liquid for glass ionomer cements (Fuji Ionomer Type I Liquid sold from G-C Dental Industrial Corp. and produced under batch No. 120641) in a proportion of 1.4 g to 1.0 g for the measurement of physical properties. Consistency, working time, initial setting time, crushing strength, rate of disintegration and rate of disintegration just after the initial setting, measured by the procedures of Ex. 1, were 27 mm, 1 minute 30 seconds, 5 minutes 30 seconds, 1350±70 Kg/cm$^2$, 0.65% and 1.52%, respectively. The products of Examples 1 to 8 were found to be superior in all the physical properties to those of Comparative Example 1 and excellent as the dental luting cements.

Comparative Example 2

One hundred (100) g of the glass powders of Comparative Example 1 were mixed with 100 g of an 1% aqueous solution of potassium hexafluorotitanate to make a slurry, which was then surface-treated by drying it in a dryer having a temperature of 120° C. for the evaporation of moisture. The thus obtained powders were then mixed with a commercially available setting liquid for glass ionomer cements (Fuji Ionomer Type I Liquid sold from G-C Dental Industrial Corp. and produced under batch No. 120641) in a proportion of 1.5 g to 1.0 g. Consistency, working time, initial setting time, crushing strength, rate of disintegration and rate of disintegration just after the initial setting, determined by the procedures of Ex. 1, were respectively 28 mm, 1 minute 45 seconds, 6 minutes 00 second, 1470±80 Kg/cm$^2$, 0.40% and 1.22%. The dental luting cements according to Examples 1 to 10 are found to be improved in the physical properties over those of Comparative Example 2.

Comparative Example 3

Cement powders and a setting liquid similar to those used in Comparative Example 2 were provided and mixed together in a proportion of 2.2 g powders to 1.0 g liquid to obtain the consistency fit for filling. The physical properties were determined as in Examples 11 to 14.

Consistency, working time, initial setting time, crushing strength, rate of disintegration and rate of disintegration just after the initial setting were respectively 30 mm, 2 minutes 20 seconds, 4 minutes 15 seconds, 1680±100 Kg/cm$^2$, 0.32% and 0.75%. It is believed that the products of Examples 11 to 14 are cements excellent for dental filling which are superior in all the physical properties to those of Comparative Example 3.

Experimental Example 1

The mixed cement paste of Examples 1 to 10 and Comparative Example 1 was hardened to a thickness of 1 mm, while teeth were cut to a thickness of 1 mm. Roentogenographs were taken of the samples with a roentgenographical device for dental purposes to compare them as regards the radio-opacity. As a result, it was found that the products of Examples 1 to 10 showed stronger radio-opacity than did the enamel of teeth, whereas the product of Comparative Example 1 showed no radio-opacity at all.

What is claimed is:

1. A fluoroaluminosilicate glass powder for dental glass ionomer cements, which has a specific gravity of 2.4 to 3.5 and a mean particle size of 0.02 to 10 μm and which, in its components, consists essentially of 20 to 50% by weight of SiO$_2$, 20 to 40% by weight of Al$_2$O$_3$, 15 to 40% by weight of SrO, 1 to 20% by weight of F$_2$ and 0 to 15% by weight of P$_2$O$_5$ on the converted oxide basis, and are free from Li, Na, K, Rb, Cs, Be, Mg and Ba ions.

2. A fluoroaluminosilicate glass powder for dental glass ionomer cements, which has a specific gravity of 2.4 to 3.5 and a mean particle size of 0.02 to 10 μm and which, in its components, consists essentially of 20 to 50% by weight of SiO$_2$, 20 to 40% by weight of Al$_2$O$_3$, 15 to 40% by weight of SrO, 1 to 20% by weight of F$_2$ and 0 to 15% by weight of P$_2$O$_5$ on the converted oxide basis, and are free from Li, Na, K, Rb Cs, Be, Mg, Ca and Ba ions.

3. A fluoroaluminosilicate glass powder for dental glass ionomer cements, which has a specific gravity of 2.4 to 3.5 and a mean particle size of 0.02 to 10 μm and which, in its components, consists essentially of 20 to 50% by weight of SiO$_2$, 20 to 40% by weight of Al$_2$O$_3$, 15 to 40% by weight of SrO, 1 to 20% by weight of F$_2$ and 0 to 15% by weight of P$_2$O$_5$ on the converted oxide basis, and free from Li, Na, K, Rb Cs, Be, Mg and Ba ions, wherein 100 parts by weight of said glass powder are treated on its surface with an acid and/or a fluoride so as to leave 0.01 to 5 parts by weight of a residue.

4. A fluoroaluminosilicate glass powder for dental glass ionomer cements, which has a specific gravity of 2.4 to 3.5 and a mean particle size of 0.02 to 10 μm and which, in its components, consists essentially of 20 to 50% by weight of SiO$_2$, 20 to 40% by weight of Al$_2$O$_3$, 15 to 40% by weight of SrO, 1 to 20% by weight of F$_2$ and 0 to 15% by weight of P$_2$O$_5$ on the converted oxide basis and free from Li, Na, K, Rb Cs, Be, Mg, Ca and Ba ions, wherein 100 parts by weight of said glass powder are treated on its surface with an acid and/or a fluoride so as to leave 0.01 to 5 parts by weight of a residue.

5. A fluoroaluminosilicate glass powder according to claim 3, wherein said glass powder is treated on its surface with a fluoride.

6. A fluoroaluminosilicate glass powder according to claim 4, wherein said glass powder is treated on its surface with a fluoride.

* * * * *